US008809569B2

(12) United States Patent
Zhang et al.

(10) Patent No.: US 8,809,569 B2
(45) Date of Patent: Aug. 19, 2014

(54) PROCESS FOR PREPARING DIALKYL CARBONATE AND DIOL PRODUCTS

(75) Inventors: Xiankuan Zhang, Houston, TX (US); Ray Montez, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 13/406,711

(22) Filed: Feb. 28, 2012

(65) Prior Publication Data

US 2013/0225850 A1 Aug. 29, 2013

(51) Int. Cl.
*C07C 68/06* (2006.01)
*C07C 69/96* (2006.01)
*C07D 317/36* (2006.01)
*C07D 317/38* (2006.01)

(52) U.S. Cl.
CPC .................. *C07C 68/06* (2013.01); *C07C 69/96* (2013.01); *C07D 317/36* (2013.01); *C07D 317/38* (2013.01)
USPC ........................................................ 558/277

(58) Field of Classification Search
None
See application file for complete search history.

(56) References Cited

U.S. PATENT DOCUMENTS

| | | | |
|---|---|---|---|
| 4,691,041 A | 9/1987 | Duranleau et al. | |
| 5,359,118 A | 10/1994 | Wagner et al. | |
| 5,648,508 A | 7/1997 | Yaghi | |
| 6,479,689 B1 | 11/2002 | Tojo et al. | |
| 6,617,467 B1 | 9/2003 | Muller et al. | |
| 6,624,318 B1 | 9/2003 | Muller et al. | |
| 7,084,292 B2 | 8/2006 | Buchanan et al. | |
| 7,119,219 B2 | 10/2006 | Mueller et al. | |
| 7,435,842 B2 | 10/2008 | Miyake et al. | |
| 7,446,218 B2 | 11/2008 | Miyake et al. | |
| 7,556,673 B2 | 7/2009 | Schubert et al. | |
| 7,652,122 B2 | 1/2010 | Miyake et al. | |
| 7,663,005 B2 | 2/2010 | Crudge et al. | |
| 7,842,827 B2 | 11/2010 | Schubert et al. | |
| 7,879,221 B2 | 2/2011 | Putter et al. | |
| 7,880,026 B2 | 2/2011 | Ni et al. | |
| 7,910,732 B2 | 3/2011 | Schubert et al. | |
| 7,968,739 B2 | 6/2011 | Mueller et al. | |
| 2003/0023109 A1 | 1/2003 | Schlosberg et al. | |
| 2003/0045739 A1 | 3/2003 | Buchanan et al. | |
| 2008/0300431 A1 | 12/2008 | Crudge et al. | |

FOREIGN PATENT DOCUMENTS

| | | | |
|---|---|---|---|
| EP | 1125915 A1 | 8/2001 | |
| JP | 2003342233 A | 12/2003 | |

OTHER PUBLICATIONS

Amberlite IRA-904 Technical Notes, Rohm and Haas, Sep. 1979.

Accessed Sep. 23, 2013 from <http://www4.mpbio.com/ecom/docs/proddata.nsf/9940ff31a5dd2f94852570c80058617b/47972db03a26de3385256dde0075ac01/$FILE/150322.pdf>.*
International Search Report in International Counterpart Application No. PCT/US2012/070551, Jun. 25, 2013, pp. 1-7.
Written Opinion of the International Searching Authority in International Counterpart Application No. PCT/US2012/070551, Jun. 25, 2013, pp. 1-12.
PCT/ISA/206 Invitation to Pay Additional Fees with Annex.—Communication Relating to the Results of the Partial International Search in PCT/US2012/070551, Mar. 27, 2013, pp. 1-7.
Song, J., Zhang, et al., Synthesis of cyclic carbonates and dimethyl carbonate using CO2 as a building block catalyzed by MOF-5/Kl and MOF-5/Kl/K2CO, Frontiers of Chemistry in in China 6 (1), Mar. 2011, pp. 21-30.
Song, J., Zhang, Z., Hu, S., Wu, T., Jiang, T., Han, B., "MOF-5/n-Bu4NBr: An efficient catalyst system for the synthesis of cyclic carbonates from epoxides and CO2 under mild conditions", Green Chemistry, vol. 11, Issue 7, 2009, pp. 1031-1036.
Zhou, Y., Song, J., Liang, S., Hu, S., Liu, H., Jiang, T., Han, B., "Metal-organic frameworks as an acid catalyst for the synthesis of ethyl methyl carbonate via transesterification", Journal of Molecular Catalysis A: Chemical 308 (1-2), Aug. 2009, pp. 68-72.
Li, Y., Tang, Z.-G., Zhu, J.-Q., Fei, W.-Y. , "CO2 solubility in dimethyl carbonate and its intensification approaches", Huaxue Gongcheng/Chemical Engineering (China) 38 (8), Aug. 2010, pp. 69-72 (English Abstract Only).
Chang, Y., Jiang, T., Han, B., Liu, Z., Wu, W., Gao, L., Li, J., Gao, H., Zhao, G., Huang, J., "One-pot synthesis of dimethyl carbonate and glycols from supercritical CO2, ethylene oxide or propylene oxide, and methanol", Applied Catalysis A: General, vol. 263, Issue 2, Jun. 10, 2004, pp. 179-186.
Song, J., Zhang, Z., Han, B., Hu, S., Li, W., Xie, Y., "Synthesis of cyclic carbonates from epoxides and CO2 catalyzed by potassium halide in the presence of β-cyclodextrin", Green Chemistry vol. 10, Issue 12, 2008, pp. 1337-1341.

(Continued)

*Primary Examiner* — Alicia L Otton
(74) *Attorney, Agent, or Firm* — Cantor Colburn LLP

(57) ABSTRACT

Dialkyl carbonate and diol products are prepared in an integrated process performed by reacting an alkylene oxide with carbon dioxide in the presence of a non-halide-containing homogeneous carbonation catalyst in a first reaction zone to form a crude cyclic carbonate product. The crude cyclic carbonate product is introduced along with an aliphatic monohydric alcohol to a second reaction zone containing a transesterification catalyst. The transesterification catalyst is comprised of a strongly basic Type I ion exchange resin in gel having a particular form. The cyclic carbonate product and monohydric alcohol are reacted to form the dialkyl carbonate and diol products. In another aspect, dialkyl carbonate and diol products are prepared in an integrated process wherein a halide-containing homogeneous carbonation catalyst is used to form a crude cyclic carbonate product that is then used in a transesterification reaction. The transesterification catalyst is regenerated to accommodate the effects of the halide-containing catalyst.

13 Claims, 4 Drawing Sheets

(56) References Cited

OTHER PUBLICATIONS

Liang, S., Liu, H., Jiang, T., Song, J., Yang, G., Han, B., "Highly efficient synthesis of cyclic carbonates from CO2 and epoxides over cellulose/KI", Chemical Communications vol. 47, Issue 7, Feb. 21, 2011, pp. 2131-2133.

Jiang, J.-I., Hua, R., "Synthesis of Dimethyl Carbonate from CO2, Methanol, and Epoxides Using Re(CO)5 Cl/K2 CO3 as Catalyst System", Chemical Research in Chinese Universities vol. 23, Issue 3, May 2007, pp. 374-376.

Song, Z., Li, G.-H., Yu, Y., Shi, Z., Feng, S.-H., "Hydrothermal Synthesis and Structural Characterization of Three-dimensional Metal-organic Framework [Zn3(C2H2N3)2(C7H5O2)4]", Chemical Research in Chinese Universities, vol. 25, Issue 1, 2009, pp. 1-4.

Tian, J.-S., Miao, C.-X., Wang, J.-Q., Cai, F., Du, Y., Zhao, Y., He, L.-N., "Efficient synthesis of dimethyl carbonate from methanol, propylene oxide and CO2 catalyzed by recyclable inorganic base/phosphonium halide-functionalized polyethylene glycol", Green Chemistry, vol. 9, Issue 6, 2007, pp. 566-571.

IonPac® AS21 Anion-Exchange Column Information Sheet, Dionex Corporation, Copyright Date Listed 2005, pp. 1-4.

Purolite Ion Exchange Resin Technical Data Sheet, no date listed, accessed Feb. 23, 2012, pp. 1-8.

\* cited by examiner

PROCESS FOR PREPARING DIALKYL CARBONATE AND DIOL PRODUCTS

FIELD OF THE INVENTION

The present invention relates to methods for preparing dialkyl carbonate and diol products from alkylene oxide in an integrated process.

BACKGROUND

Monoethylene glycol (MEG), often referred to as ethylene glycol, is an important compound that is often used in antifreeze and in the production of certain polymers, such as polyester and polyethylene terephthalate, which is commonly used in plastic bottles for soft drinks. Ethylene glycol may be produced by the reaction of ethylene oxide and water. Various byproducts, such as di-ethylene glycol (DEG), tri-ethylene glycol (TEG), etc., are often co-produced using this synthesis method, so that yields of monoethylene glycol may be lower than desired. As used herein, the expression "ethylene glycol" without any prefix is meant to encompass monoethylene glycol, unless otherwise stated or is apparent from its context.

Another method of forming ethylene glycol is from ethylene carbonate (EC). Ethylene carbonate may be converted to dimethyl carbonate (DMC) and ethylene glycol in the presence of methanol in a transesterification reaction. Using such reaction method, the yield of ethylene glycol is much higher, with less undesirable byproducts being produced. Additionally, the product dimethyl carbonate produced in such reaction is useful as an oxygenate additive in fuel and in the production of Bisphenol A, which is commonly used in making polycarbonate plastics and epoxy resins.

The ethylene carbonate used in producing ethylene glycol and dimethyl carbonate may be prepared from ethylene oxide in a carbonation reaction. The carbonation of ethylene oxide with carbon dioxide ($CO_2$) yields ethylene carbonate. The use of carbon dioxide as a reactant may be particularly desirable due to the increased emphasis presently placed on minimizing $CO_2$ emissions.

To yield ethylene glycol in the transesterification reaction, a purified source of ethylene carbonate is typically used. Recently, however, integrated processes have been developed that utilize ethylene oxide and $CO_2$ in a first carbonation stage to yield a crude or unpurified ethylene carbonate product, which is then used in a second transesterification stage wherein the ethylene carbonate product is converted to ethylene glycol and dimethyl carbonate. One such integrated process is described, for instance, in U.S. Pat. No. 7,084,292.

Although an integrated process eliminates the need for a purified ethylene carbonate source, one of the issues with an integrated process is the effect of the catalyst used in the carbonation reaction on the transesterification reaction. Homogeneous catalysts are often used for the carbonation reaction. Without purification of the ethylene carbonate product to remove the homogeneous catalyst, the homogeneous catalyst is carried with the ethylene carbonate product into the reaction zone used for transesterification. The homogeneous catalyst can have a negative impact on the transesterification catalyst.

Accordingly, improvements are needed to provide an integrated carbonation/transesterification process for the production of ethylene glycol and/or dimethyl carbonate, and similar products, which overcomes these issues.

SUMMARY

A method of preparing a dialkyl carbonate and diol products in an integrated process is accomplished by reacting an alkylene oxide with carbon dioxide in the presence of a non-halide-containing homogeneous carbonation catalyst in a first reaction zone to form a crude cyclic carbonate product. The crude cyclic carbonate product from the first reaction zone is introduced along with an aliphatic monohydric alcohol to a second reaction zone containing a transesterification catalyst. The transesterification catalyst is a strongly basic Type I ion exchange resin preferably in gel form of polystyrene crosslinked with divinyl benzene having preferably from about 4% to about 8% crosslinking, and preferably from about 40% to about 60% water retention. The ion exchange resin preferably includes at least one of quaternary ammonium groups or quaternary phosphonium groups. The transesterification catalyst is preferably configured as substantially spherical beads having a particle size of from about 0.2 mm to about 1.5 mm. The cyclic carbonate product and monohydric alcohol are allowed to react under reaction conditions to form the dialkyl carbonate and diol products.

In certain embodiments, the alkylene oxide has the formula

wherein $R_1$ and $R_2$ are independently from one another a $—(CH_2)_m—$ group, wherein m is an integer of from 1 to 3, more particularly 1 to 2. The aliphatic monohydric alcohol may be a $C_1$ to $C_5$ aliphatic monohydric alcohol. In specific embodiments, the alkylene oxide may be ethylene oxide and the monohydric alcohol may be methanol. In such cases, the dialkyl carbonate may includes dimethyl carbonate and the diol may include monoethylene glycol.

The non-halide-containing homogeneous catalyst may be selected from at least one of KOH, $K_2CO_3$, and $KHCO_3$, potassium methoxide ($KOCH_3$), benzyltrimethylammonium hydroxide, and $(C_2H_5)_4NO$ in certain applications. The non-halide-containing homogeneous catalyst is preferably used in an amount of from about 0.01% to about 5% by weight of alkylene oxide that is introduced into the first reaction zone.

The molar ratio of aliphatic monohydric alcohol to the crude cyclic carbonate product introduced into the second reaction zone is preferably from about 1.5:1 to about 3:1.

The ion exchange resin may include an anion selected from the group consisting of bicarbonate, bisulfite, metalate, carboxylate, and halide.

In a further embodiment, unreacted alkylene oxide, unreacted carbon dioxide, or both, are removed from said crude cyclic carbonate product prior to introducing the crude cyclic carbonate product to the second reaction zone.

In another method of preparing a dialkyl carbonate and diol products in an integrated process, the steps (a) through (c) are performed. In (a), an alkylene oxide is reacted with carbon dioxide in the presence of a halide-containing homogeneous carbonation catalyst in a first reaction zone to form a crude cyclic carbonate product, the crude cyclic carbonate product containing amounts of the carbonation catalyst. In (b), the crude cyclic carbonate product from the first reaction zone is introduced along with an aliphatic monohydric alcohol to a second reaction zone containing a transesterification catalyst comprised of an ion exchange resin. The cyclic carbonate product and monohydric alcohol are allowed to react under reaction conditions to form the dialkyl carbonate and diol products until the ion exchange resin catalyst has deactivated to a selected degree. In (c), the deactivated ion exchange resin of the second reaction zone is regenerated by washing the ion exchange resin with water and contacting the washed ion exchange resin with a regeneration solution containing regenerating ions before continuing step (b).

In certain embodiments, the halide-containing homogeneous carbonation catalyst is a $C_1$ to $C_5$ organic halide compound. The alkylene oxide has the formula

wherein $R_1$ and $R_2$ are independently from one another a $-(CH_2)_m-$ group, wherein m is an integer of from 1 to 3, more particularly 1 to 2.

The aliphatic monohydric alcohol may be a $C_1$ to $C_5$ aliphatic monohydric alcohol. The alkylene oxide may be ethylene oxide and the monohydric alcohol may be methanol. In such instances, the dialkyl carbonate includes dimethyl carbonate and the diol includes monoethylene glycol.

The halide-containing homogeneous catalyst may be selected from at least one of alkali halide salts, quaternary ammonium halide compounds, organic amine halide compounds, and phosphine halide compounds. The halide-containing homogeneous catalyst is preferably used in an amount of from about 0.01% to about 5% by weight of alkylene oxide that is introduced into the first reaction zone.

The molar ratio of aliphatic monohydric alcohol to the crude cyclic carbonate product introduced into the second reaction zone is preferably from about 1.5:1 to about 3:1.

In certain embodiments, the ion exchange resin may be a strongly basic Type I ion exchange resin preferably in gel form of polystyrene crosslinked with divinyl benzene having preferably from about 4% to about 8% crosslinking, and preferably from about 40% to about 60% water retention. The ion exchange resin may include at least one of quaternary ammonium groups or quaternary phosphonium groups. The transesterification catalyst may be configured as substantially spherical beads having a particle size of preferably from about 0.2 mm to about 1.5 mm. In certain instances, the ion exchange resin may include an anion selected from the group consisting of bicarbonate, bisulfite, metalate, carboxylate, and halide.

In a further embodiment, unreacted alkylene oxide, unreacted carbon dioxide, or both, are removed from said crude cyclic carbonate product of step (a) prior to introducing the crude cyclic carbonate product to the second reaction zone in step (b).

In still another embodiment, a method of preparing a dialkyl carbonate and diol products in an integrated process is accomplished by reacting an alkylene oxide with carbon dioxide in the presence of a non-halide-containing homogeneous carbonation catalyst in a first reaction zone to form a crude cyclic carbonate product. The crude cyclic carbonate product from the first reaction zone is introduced along with an aliphatic monohydric alcohol to a second reaction zone containing a transesterification catalyst. The transesterification catalyst is a strongly basic Type I ion exchange resin preferably in gel form of polystyrene crosslinked with divinyl benzene having preferably from 4% to 8% crosslinking, and preferably from 40% to 60% water retention. The ion exchange resin preferably includes at least one of quaternary ammonium groups or quaternary phosphonium groups. The transesterification catalyst is preferably configured as substantially spherical beads having a particle size of from 0.2 mm to 1.5 mm. The cyclic carbonate product and monohydric alcohol are allowed to react under reaction conditions to form the dialkyl carbonate and diol products.

In certain embodiments, the alkylene oxide has the formula

wherein $R_1$ and $R_2$ are independently from one another a $-(CH_2)_m-$ group, wherein m is an integer of from 1 to 3, more particularly 1 to 2. The aliphatic monohydric alcohol may be a $C_1$ to $C_5$ aliphatic monohydric alcohol. In specific embodiments, the alkylene oxide may be ethylene oxide and the monohydric alcohol may be methanol. In such cases, the dialkyl carbonate may includes dimethyl carbonate and the diol may include monoethylene glycol.

The non-halide-containing homogeneous catalyst may be selected from at least one of KOH, $K_2CO_3$, and $KHCO_3$, potassium methoxide ($KOCH_3$), benzyltrimethylammonium hydroxide, and $(C_2H_5)_4NO$ in certain applications. The non-halide-containing homogeneous catalyst is preferably used in an amount of from 0.01% to 5% by weight of alkylene oxide that is introduced into the first reaction zone.

The molar ratio of aliphatic monohydric alcohol to the crude cyclic carbonate product introduced into the second reaction zone is preferably from 1.5:1 to 3:1.

The ion exchange resin may include an anion selected from the group consisting of bicarbonate, bisulfite, metalate, carboxylate, and halide.

In a further embodiment, unreacted alkylene oxide, unreacted carbon dioxide, or both, are removed from said crude cyclic carbonate product prior to introducing the crude cyclic carbonate product to the second reaction zone.

In another method of preparing a dialkyl carbonate and diol products in an integrated process, the steps (a) through (c) are performed. In (a), an alkylene oxide is reacted with carbon dioxide in the presence of a halide-containing homogeneous carbonation catalyst in a first reaction zone to form a crude cyclic carbonate product, the crude cyclic carbonate product containing amounts of the carbonation catalyst. In (b), the crude cyclic carbonate product from the first reaction zone is introduced along with an aliphatic monohydric alcohol to a second reaction zone containing a transesterification catalyst comprised of an ion exchange resin. The cyclic carbonate product and monohydric alcohol are allowed to react under reaction conditions to form the dialkyl carbonate and diol products until the ion exchange resin catalyst has deactivated to a selected degree. In (c), the deactivated ion exchange resin of the second reaction zone is regenerated by washing the ion exchange resin with water and contacting the washed ion exchange resin with a regeneration solution containing regenerating ions before continuing step (b).

In certain embodiments, the halide-containing homogeneous carbonation catalyst is a $C_1$ to $C_5$ organic halide compound. The alkylene oxide has the formula

wherein $R_1$ and $R_2$ are independently from one another a $-(CH_2)_m-$ group, wherein m is an integer of from 1 to 3, more particularly 1 to 2.

The aliphatic monohydric alcohol may be a $C_1$ to $C_5$ aliphatic monohydric alcohol. The alkylene oxide may be ethylene oxide and the monohydric alcohol may be methanol. In such instances, the dialkyl carbonate includes dimethyl carbonate and the diol includes monoethylene glycol.

The halide-containing homogeneous catalyst may be selected from at least one of alkali halide salts, quaternary ammonium halide compounds, organic amine halide compounds, and phosphine halide compounds. The halide-containing homogeneous catalyst is preferably used in an amount of from 0.01% to 5% by weight of alkylene oxide that is introduced into the first reaction zone.

The molar ratio of aliphatic monohydric alcohol to the crude cyclic carbonate product introduced into the second reaction zone is preferably from 1.5:1 to 3:1.

In certain embodiments, the ion exchange resin may be a strongly basic Type I ion exchange resin preferably in gel form of polystyrene crosslinked with divinyl benzene having preferably from 4% to 8% crosslinking, and preferably from 40% to 60% water retention. The ion exchange resin may include at least one of quaternary ammonium groups or quaternary phosphonium groups. The transesterification catalyst may be configured as substantially spherical beads having a particle size of preferably from 0.2 mm to 1.5 mm. In certain instances, the ion exchange resin may include an anion selected from the group consisting of bicarbonate, bisulfite, metalate, carboxylate, and halide.

In a further embodiment, unreacted alkylene oxide, unreacted carbon dioxide, or both, are removed from said crude cyclic carbonate product of step (a) prior to introducing the crude cyclic carbonate product to the second reaction zone in step (b).

BRIEF DESCRIPTION OF THE DRAWINGS

For a more complete understanding of the present invention, and the advantages thereof, reference is now made to the following descriptions taken in conjunction with the accompanying figures, in which.

DETAILED DESCRIPTION

Figure 1:
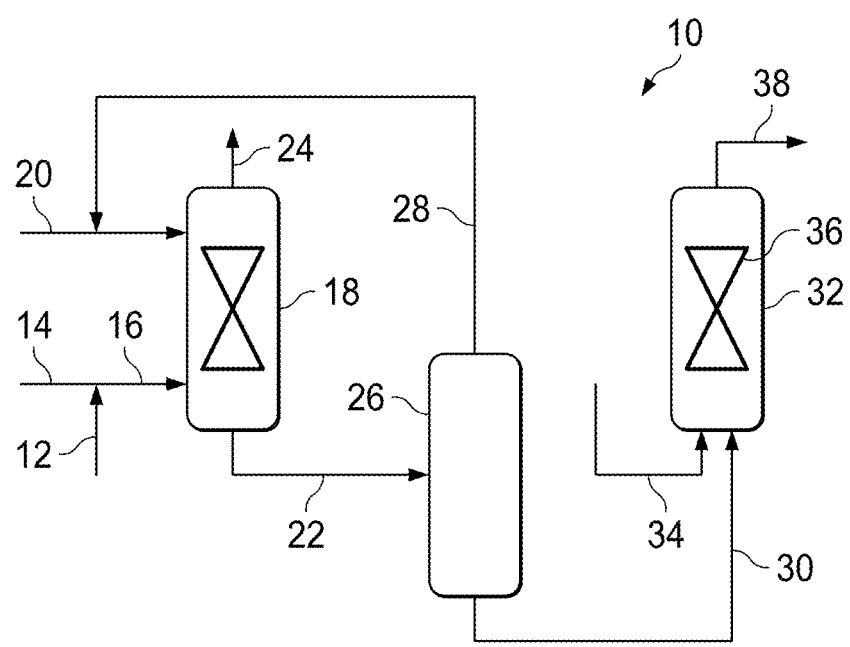
FIG. 1 is a schematic of integrated process system for producing dimethyl carbonate and ethylene glycol from ethylene oxide starting materials using homogeneous carbonation catalysts and an ion exchange resin transesterification catalyst.

In preparing dialkyl carbonate and diol products in an integrated process according to the invention, the first stage involves the carbonation of an alkylene oxide with carbon dioxide. In many applications the alkylene oxide will be ethylene oxide, which is then used to prepare ethylene carbonate in the carbonation reaction. The alkylene oxide may include other compounds, such as propylene oxide, however, other alkylene oxides may also be used for the preparation of dialkyl carbonate and diol products. Generally, the alkylene oxide may have the Formula (1) below:

(1)

wherein $R_1$ and $R_2$ are independently from one another a $-(CH_2)_m-$ group, wherein m is an integer of from 1 to 3, more particularly 1 to 2.

In the integrated process, the alkylene oxide is reacted with carbon dioxide ($CO_2$) in a carbonation reactor. The reaction may be illustrated by the following Equation (2) below:

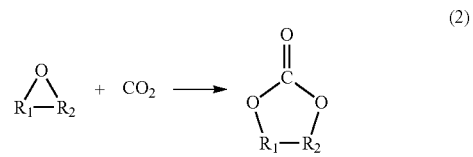

(2)

wherein $R_1$ and $R_2$ are the same as described for Formula (1). The above reaction constitutes the carbonation reaction and also shows the stoichiometric numbers for the reaction and the product.

The carbon dioxide used in the carbonation may be a purified carbon dioxide source, however, other non-purified sources of carbon dioxide may be used. Impurities in such non-purified carbon dioxide source may include nitrogen, oxygen, hydrogen, carbon monoxide, nitric oxide, and light hydrocarbons. The carbon dioxide may be used in approximately stoichiometric amount with the alkylene oxide. In many instances an excess of carbon dioxide may also be used with a $CO_2$/alkylene oxide molar feed ratio ranging from greater than 1 to about 2. However, other ratios may also be used. The amount of carbon dioxide used in the carbonation may be adjusted as necessary to provide the optimum reaction performance and conversion. Additionally, the carbon dioxide feed used in the carbonation reaction may be, at least in part, a recycled carbon dioxide, as is described later on.

It should be understood that with respect to any concentration or amount range listed or described herein as being useful, suitable, or the like, it is intended to include every concentration or amount within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range.

In the present invention, the carbonation catalyst is a homogeneous catalyst, wherein the catalyst is present in the same phase as the alkylene oxide reactant. The homogeneous catalyst may be a non-halide-containing catalyst or a halide-containing catalyst. As will be described in more detail later on, halide-containing catalysts can affect ion exchange resin catalysts used in the transesterification reaction, requiring certain regeneration procedures to be used.

The homogeneous non-halide-containing catalysts may include inorganic and organic compounds. Combinations of different non-halide-containing homogeneous catalysts may be used, both inorganic and organic.

The non-halide inorganic compounds may include various alkali compounds, such as the hydroxides, carbonates and bicarbonates of alkali metals. Potassium compounds in particular may be well suited for use as the non-halide-containing carbonation catalyst. Such potassium compounds may include KOH, $K_2CO_3$, and $KHCO_3$, which are all strong bases. The foregoing list is not exhaustive, and other catalysts may be useful.

Non-halide-containing organic compounds may also be used as the homogeneous carbonation catalyst. Such organic compounds may include quaternary ammonium compounds, for example the hydroxides, carbonates and bicarbonates of such quaternary ammonium compounds. Non-limiting examples of various non-halide organic compounds suitable for use as carbonation catalysts include the alkali methoxides (e.g. $KOCH_3$), alkali ethoxides (e.g. $KOC_2H_5$), and benzyltrimethylammonium hydroxide. Various non-halide-containing quaternary ammonium compounds suitable for use as carbonation catalysts are also described, for example, in U.S. Pat. App. Pub. No. US2003/0023109A1, which is incorporated herein by reference for all purposes.

In other embodiments of the invention, a halide-containing homogeneous carbonation catalyst is used. The halide-containing catalyst may include inorganic salts and organic halides. Combinations of different halide-containing homogeneous catalysts may be used, both inorganic and organic. In certain instances, the halide-containing homogeneous catalyst may be those that contain halides other than iodine.

The inorganic halide salts may include the alkali halides. Potassium halides have been found particularly useful, such as KCl, KBr, and KI. Other alkali halide salts may also be suitable, with the activity of the salt being related to its basicity. Alkali earth metal and rare earth metal halides may also be useful.

Organic halide compounds may also be used for the halide-containing carbonation catalyst. Various organic halide compounds can be used for the homogenous carbonation catalysts. These may include organic halides having organic groups containing from 1 to 5 carbon atoms or more. The organic halides may include quaternary ammonium, organic amine, and phosphine halide compounds. Non-limiting examples of such compounds include tetraethylammonium bromide $((C_2H_5)_4BrNBr)$, tetrabutylphosphonium bromide $((C_4H_9)_4PBr)$, tetrabutylphospnoium iodide $((C_4H_9)_4PI)$, methyltrihenylphosphonium bromide $(CH_3(C_6H_5)_3PBr)$, and methyltributylphosphonium iodide $(CH_3(C_6H_5)_3PI)$. Various halide-containing homogeneous carbonation catalysts are also described, for example, in U.S. Pat. No. 7,084,292, which is incorporated herein by reference for all purposes.

The homogeneous carbonation catalyst, halide or non-halide, is typically dissolved in the alkylene oxide and fed to the carbonation reactor or reaction zone(s). The catalyst amount may vary but is typically used in an amount of from about 0.01% to about 5% by weight of the alkylene oxide feed, more particularly from about 0.05% to about 2% by weight of the alkylene oxide feed.

The carbonation reaction can be carried out in a variety of different reactors, batch or continuous. These reactors may include stir tank, continuous flow, and reactive distillation type reactors. One or more reactors, used in series or parallel, may be used for the carbonation reactions. Typical carbonation reaction conditions include a temperature range of from about 50° C. to about 250° C., with from about 150° C. to about 220° C. being typical. Reactor pressures may range from about 500 psig to about 1000 psig, more particularly from about 750 psig to about 900 psig. Carbon dioxide is typically introduced into the reactor separately from the alkylene oxide and catalyst. Reaction times may range from a few minutes (e.g. 15 min., 30 min., 60 min.) to several hours or more. It should be understood that these reaction conditions and times are merely exemplary and not exhaustive, and that other reaction conditions and times may also be suitable for use in the present invention.

The carbonation reaction products include the cyclic carbonate product, as shown in Equation (2), along with other compounds and byproducts. These may include any unreacted alkylene oxide and carbon dioxide, as well as other impurities, including amounts of the homogeneous catalyst used in the carbonation reaction. By products in the reactor effluent may include ethylene glycol, di- and tri-ethylene glycol, and higher glycols. This is particularly true in cases where water is present during the reaction, such as that may be present in any unpurified alkylene oxide feed.

In a non-integrated process, the impurities are typically removed from the cyclic carbonate product prepared in the carbonation reaction. In the present invention, however, the crude cyclic carbonate product from the carbonation reaction is used in the transesterification stage without any purification, other than the optional separation or removal of any portion of unreacted alkylene oxide and carbon dioxide, as well as any impurities of the alkylene oxide and carbon dioxide feeds. Such crude cyclic carbonate product even with such optional separation will typically contain amounts of the homogeneous catalyst. Accordingly, as used herein, the expression "integrated process" and similar expressions are meant to encompass those processes wherein the carbonation products initially prepared in such process are then used in the transesterification process or stage without any separation of byproducts or impurities, other than the optional separation or removal of unreacted alkylene oxide and carbon dioxide that can be readily removed without substantial processing or interruption of a continuous process flow. While the integrated process is particularly useful in a continuous flow process, wherein the carbonation reactor effluent is fed on continuous or substantially continuous basis to the transesterification reactor or reaction zones, it should be apparent to those skilled in the art, that temporary collection and storage of the carbonation products may still be used such that the process is not generally continuous. The integrated process is therefore also meant to encompass those non-continuous processes wherein the carbonation products may be temporarily collected and stored for a period of time, provided the carbonation products are crude carbonation products, which include amounts of the homogeneous catalyst, that are then used in the transesterification process, with only optional removal of the aforementioned alkylene oxides and carbon dioxide.

After carbonation, the crude cyclic carbonation product is further processed in a transesterification stage, wherein the cyclic carbonation product is converted to dialkyl carbonate and diol products. Typically a reagent of an aliphatic monohydric alcohol is used in the transesterification. The alcohol is typically an alcohol having a $C_1$ to $C_5$ alkyl group. The transesterification reaction is represented in stoichiometric amounts by Equation (3) below:

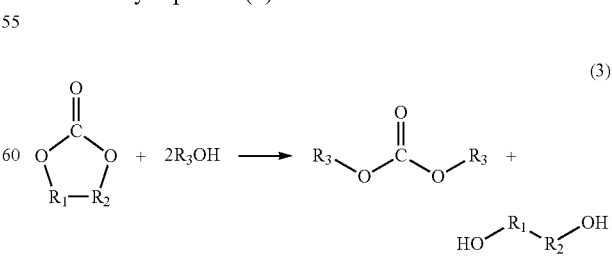

(3)

wherein $R_1$ and $R_2$ are the same as defined previously with respect to Formula (1), and $R_3$ is a $C_1$ to $C_5$ alkyl group.

The crude cyclic carbonate product will typically contain amounts of the homogeneous catalyst used in the carbonation reaction. Depending upon whether the homogeneous carbonation catalyst was a non-halogen-containing catalyst or a halogen-containing catalyst, different transesterification methods may be used.

In a particular embodiment, where non-halogen-containing homogeneous catalysts are used, a specialized ion exchange resin catalyst is used in the transesterification reaction. The ion exchange resin catalyst is a strongly basic (anionic) ion exchange resin that is a heterogeneous catalyst wherein the basic groups are quaternary ammonium or quaternary phosphinium. Anionic ion exchange resins are typically classified as strongly basic or weakly basic. Strongly basic anions include anions such as $Cl^-$ and $SO_4^-$. Strongly basic anion ion exchange resins that have quaternary ammonium or phosphium groups as the exchanging group dissociate in the same way as strong alkalis such as NaOH and KOH and exhibit strong basicity. The quaternary ammonium exchange group of such resins are so strongly basic that they dissociate into $R-N^+OH^-$ not only in acidic but even in alkaline solutions. They have ion exchange properties over the entire pH range.

The strongly basic ion exchange resins may include those classified as Type I and Type II. Type I are those with a trimethylammonium group $((R-N^+(CH_3)_3)$. Type II are those with a dimethylethanolammonium group $(R-N^+(CH_3)_2CH_2CH_2OH)$.

The ion exchange resins may be based on the copolymer of styrene and divinylbenzene, vinylpryidine, polysiloxanes, as well as other solid supports having electropositive complexing sites of an inorganic nature, such as carbon, silica, silica-alumina, zeolites, glass and clays, such as hydrotalcite. Further, immobilized complexing macrocycles such as crown ethers, etc. can be used as well as a solid support. Such ion exchange resins are described, for example, in U.S. Pat. No. 7,663,005, which is incorporated herein by reference for all purposes.

Particularly useful for use in the presence of the non-halogen-containing carbonation catalyst are those ion exchange resin catalysts that are based on a strongly basic quaternary ammonium resin that includes polystyrene that is crosslinked with divinyl benzene. The divinyl benzene in such catalysts is present in an amount of from about 2 to about 10% by weight, more particularly from about 4 to about 8% by weight, wherein the polystyrene is crosslinked with from about 4 to about 8% by weight of divinyl benzene.

The ion exchange resin employed in the present invention typically includes basic groups that are bonded to the crosslinked polystyrene resin. The basic groups that are bonded to the crosslinked polystyrene resin include quaternary ammonium or quaternary phosphonium, with quaternary ammonium groups being particularly useful.

The ion exchange resin employed in the present invention typically includes more than one anion. The anion may be selected from the group of bicarbonate, bisulfite, metalate and carboxylate anions, with a bicarbonate anion being particularly useful. When the anion is a carboxylate anion, the anion may be a polycarboxylic acid anion having in its chain molecule one or more carboxyl groups and one or more carboxylate groups, the individual carboxyl and/or carboxylate groups being separated from each other in the chain molecule by a separating group consisting of at least one atom. In certain instances, the polycarboxylic acid anion may be a citric acid derivative, more particularly a mono-anion of citric acid. In certain instances, the anion is a bicarbonate anion.

In one particular embodiment the solid ion exchange resin catalyst is a catalyst based on a quaternary ammonium resin, wherein the resin comprises a trimethylbenzyl ammonium group, and wherein the anion is a bicarbonate anion.

Because of the degree of divinyl benzene crosslinking present in the ion exchange resin, a balance is maintained between the water absorbing capacity of the resin and the elastic forces of the copolymer to keep the swollen resin in a stable moisture content. Preferably, the ion exchange resin employed in the present invention has a water retention value that is from about 30% to about 80%, with a water retention value from about 40% to about 65% being even more typical. However, it should be understood that ion exchange resins having other water retention values that may be successfully used in the present invention.

Particularly useful in the present invention is a catalyst based on the strongly basic ion exchange resins in gel form including polystyrene that is crosslinked with from about 4 to about 8 wt. % divinyl benzene crosslinking and that has from 40% to 60% water retention, with the ion exchange resin including at least one of quaternary ammonium groups or quaternary phosphonium groups. Type I gel form ion exchange resins containing trimethyl ammonium groups are particularly useful. Furthermore, the catalysts may have capacities of about 1.0 eq/L to about 1.5 eq/L, more particularly from about 1.2 eq/L to about 1.3 eq/L. Such catalysts formed so that they are configured as substantially spherical beads having a particle size of from about 0.2 mm to about 1.5 mm have provided successful transesterification when used in combination with homogeneous, non-halogen-containing carbonation catalysts.

The ion exchange resins described herein are typically employed in a catalyst bed contained in a reactor vessel. Various reactors may be used for the transesterification process, such as plug flow, batch, and reactive distillation type reactors, having one or more catalyst beds or reaction zones. Such reactors described, for example, in U.S. Pat. No. 7,663,005 may also be used for the transesterification reactions. One or more reactors, used in series or parallel, may be used for the transesterification reactions.

Typical transesterification reaction conditions include a temperature range of from about 50° C. to about 250° C., with from about 150° C. to about 220° C. being preferable. Reactor pressures may range from about 100 psig to about 1000 psig, more particularly from about 200 psig to about 500 psig. The cyclic carbonate, which is typically a solid, is typically dissolved in the aliphatic monohydric alcohol and introduced in the reactor. The aliphatic monohydric alcohol is typically used in an amount to provide an alcohol to cyclic carbonate molar feed ratio of from about 1:5 to about 3:1. A LHSV of from about 1 to about 10 $hr^{-1}$ may be used in the transesterification reactor employing the ion exchange resin catalyst. It should be understood that the reaction parameters provided are exemplary and not exhaustive and that other reaction parameters may be used.

In particular embodiments, the reactant feed streams may be fed into or near the bottom of the reactor, with reaction products flowing upwardly through the catalyst bed(s) and reactor effluent being drawn from an outlet at or near the top of the reactor. In this way, the reactant mixture flows upward through the ion exchange resin catalyst. This facilitates the collection of contaminant from being trapped in the catalyst bed, which frequently occurs with downflow reactors and may provide longer catalyst life. In other embodiments, downflow or other reactor flow directions may be used.

As has been discussed, in an integrated process wherein a crude cyclo carbonate product is used in the transesterification reaction stage, the crude cyclo carbonate product may contain amounts of the homogeneous carbonation catalysts. With respect to the effect of the homogeneous carbonation catalyst on the ion exchange resin catalysts used for transesterification, the non-halide-containing carbonation catalyst do not appear to significantly affect the ion exchange resins. The halide-containing catalysts can have impact on the ion exchange resins, however. In particular, the halide ions may tend to exchange with bicarbonate ions of the ion exchange resin. It has been observed that when using halide-containing carbonate catalysts, the ion exchange resin catalysts used for transesterification will tend to deactivate.

When using the halide-containing carbonation catalysts, the transesterification ion exchange resin catalyst can be regenerated. This is typically accomplished by washing the ion exchange with water, such as deionized (DI) water, followed by contacting the ion exchange resin with a solution containing a regenerating ion.

In the integrated process, the cyclic carbonation product is converted to dialkyl carbonate and diol products. As described earlier, in many applications the alkylene oxide used in the carbonation process is ethylene oxide, which yields ethylene carbonate. The ethylene carbonate, when reacted with methanol in the transesterification reaction yields dimethyl carbonate and ethylene glycol. In addition to these products, a large intermediate compound of hydroxypropyl methylcellulose (HEMC) is typically produced as a byproduct. When recycled back, the HEMC will further react with methanol to form dimethyl carbonate and ethylene glycol. Additionally, ethylene glycol can react to form di-ethylene glycol, as well as tri-ethylene glycol and higher glycols.

After removal of the transesterification reaction products, dialkyl carbonate and diol products can be separated from each other and other compounds using known separation techniques. Other compounds from the reactor effluent may include unreacted cyclic carbonate, unreacted alcohol, the homogeneous catalyst, and various other byproducts, such as organic oxygenates and polyglycols.

FIG. 1 shows a schematic example of an integrated process system 10 for the production of dimethylcarbonate and monoethylene glycol from ethylene oxide. Such a system may also be used for the production of other dialkyl carbonates and diols using alkylene oxide starting materials, as will be apparent to those skilled in the art. As shown in FIG. 1, homogeneous catalyst 12, which may be a halide- or non-halide containing carbonation catalyst, and ethylene oxide 14 are combined in feed stream 16 and fed into a carbonation reactor 18. Carbon dioxide 20 is also feed into the reactor 18. The reactants are fed into the reactor 18 under carbonation conditions, where the carbonation reaction takes place to convert the reactants into ethylene carbonate. The crude ethylene carbonate product is withdrawn from the reactor 18. The crude ethylene carbonate product, which will contain ethylene carbonate, and typically contains amounts of the homogeneous catalyst, unreacted ethylene oxide and other byproducts is removed from the reactor 18 through line 22. Volatile compounds may be removed from the reactor 18 through vent line 24. The crude ethylene carbonate product may optionally be passed to a separator 26 where carbon dioxide and unreacted ethylene oxide may be removed via line 28; this optional removal of unreacted reactants as shown in FIG. 1 is preferred, but is not absolutely necessary for the successful practice of the present invention.

The remaining liquid crude ethylene carbonate product is removed from separator 26 through line 30 and is passed to transesterification reactor 32. Methanol is also introduced into the reactor 32 through line 34. As shown in the system 10, the methanol 34 and crude ethylene carbonate product 30 are fed into the bottom of the reactor 32 where they may be passed upwardly through a catalyst bed or beds 36 containing the ion exchange resin catalysts described herein. Product effluent is removed from the upper end of the reactor 32 through line 38. The product effluent will contain dimethyl carbonate, monoethylene glycol, unreacted methanol, unreacted ethylene carbonate, homogeneous catalyst and other by products. The transesterification products may undergo further processing and separation to remove product and to allow recycle of various compounds using known techniques.

The following examples better serve to illustrate the invention.

EXAMPLES

Example 1

To determine the effect of various homogeneous carbonation catalysts on ion exchange resin transesterification catalysts various homogeneous catalysts were tested. The homogeneous catalysts consisted of KI, $KOCH_3$, KBr and tetraethylammonium bromide. The transesterification catalyst was based on a commercially available ion exchange resin available as Global Value AS-71. This was a strongly basic Type I anion ion exchange resin in gel form that includes polystyrene crosslinked with divinyl benzene at approximately 7% crosslinking, and that has approximatley 40-60% water retention. The catalyst was formed as spherical beads having a bead size of from 0.3 to 1.3 mm.

The typical transesterification reaction conditions were those set forth in Table 1 below:

TABLE 1

| Conditions | Typical |
| --- | --- |
| Catalyst (ml) for heterogeneous process | 15 |
| Catalyst (wt %) for homogeneous process | 0.02 |
| LHSV ($hr^{-1}$) for heterogeneous process | 4 |
| Feed Flow (ml/min) | 1.0 |
| Feed: $CH_3OH$/EC (molar) | 4 |
| Temperature (° C.) for heterogeneous | 120 |
| Temperature (° C.) for homogeneous | 160 |
| Pressure (psig) | 300 |

Figure 2:
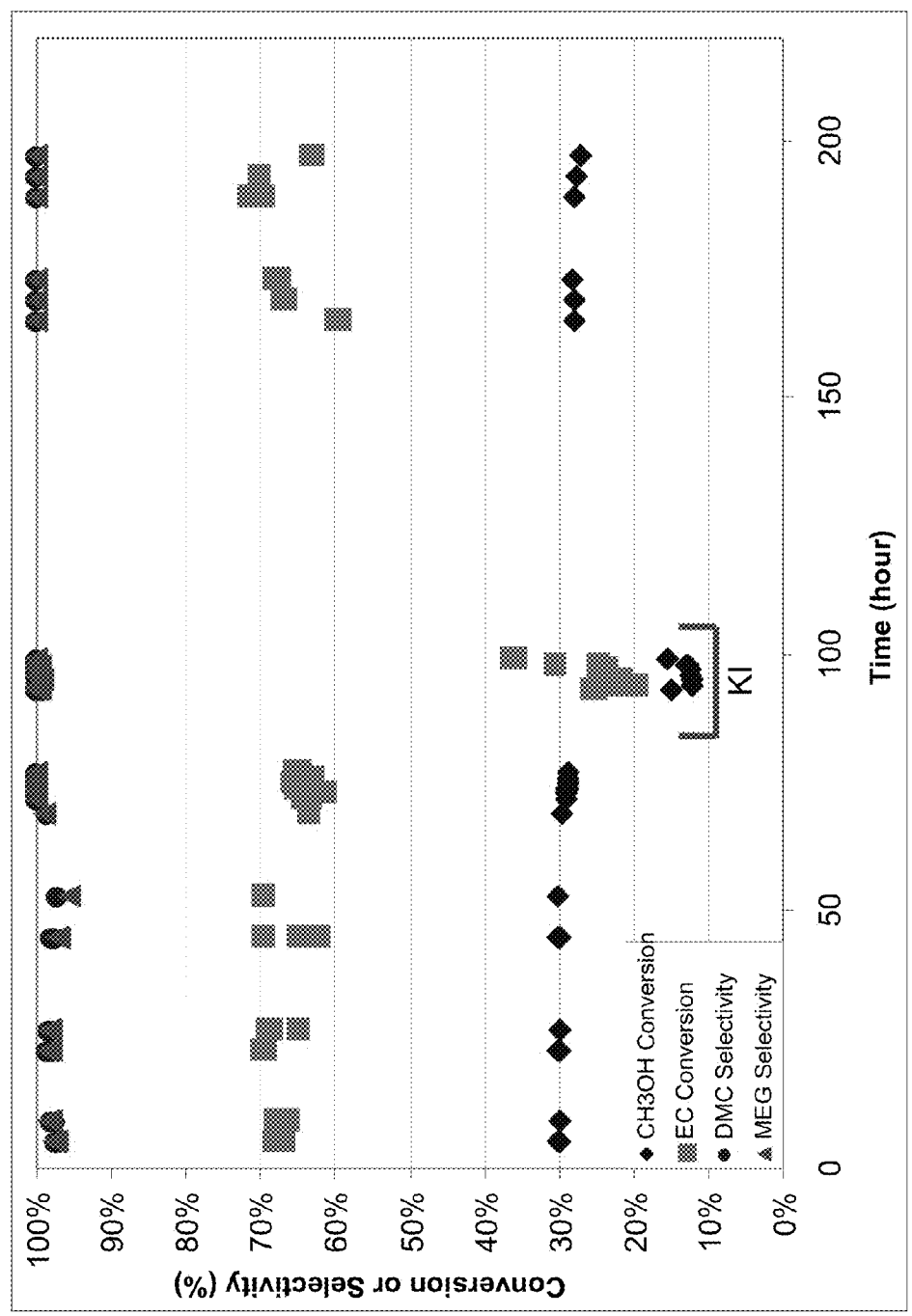
FIG. 2 is a plot of the conversion and selectivity of ethylene carbonate to dimethyl carbonate and ethylene glycol in a transesterification reaction using an ion exchange resin wherein KI is introduced into the reaction.

Initially the transesterification reactions were carried out without any homogenous catalyst in the feed. After a period of time the different homogeneous carbonation catalysts were added to the feed. As shown in FIG. 2, KI at about 0.2% by weight was added to the feed. As can be seen, the catalyst activity was reduced by more than 50% with the presence of KI in the feed. When KI was removed from the feed (i.e. a new feed without KI was added) the catalyst performance was restored almost to the level of fresh catalyst.

Figure 3:
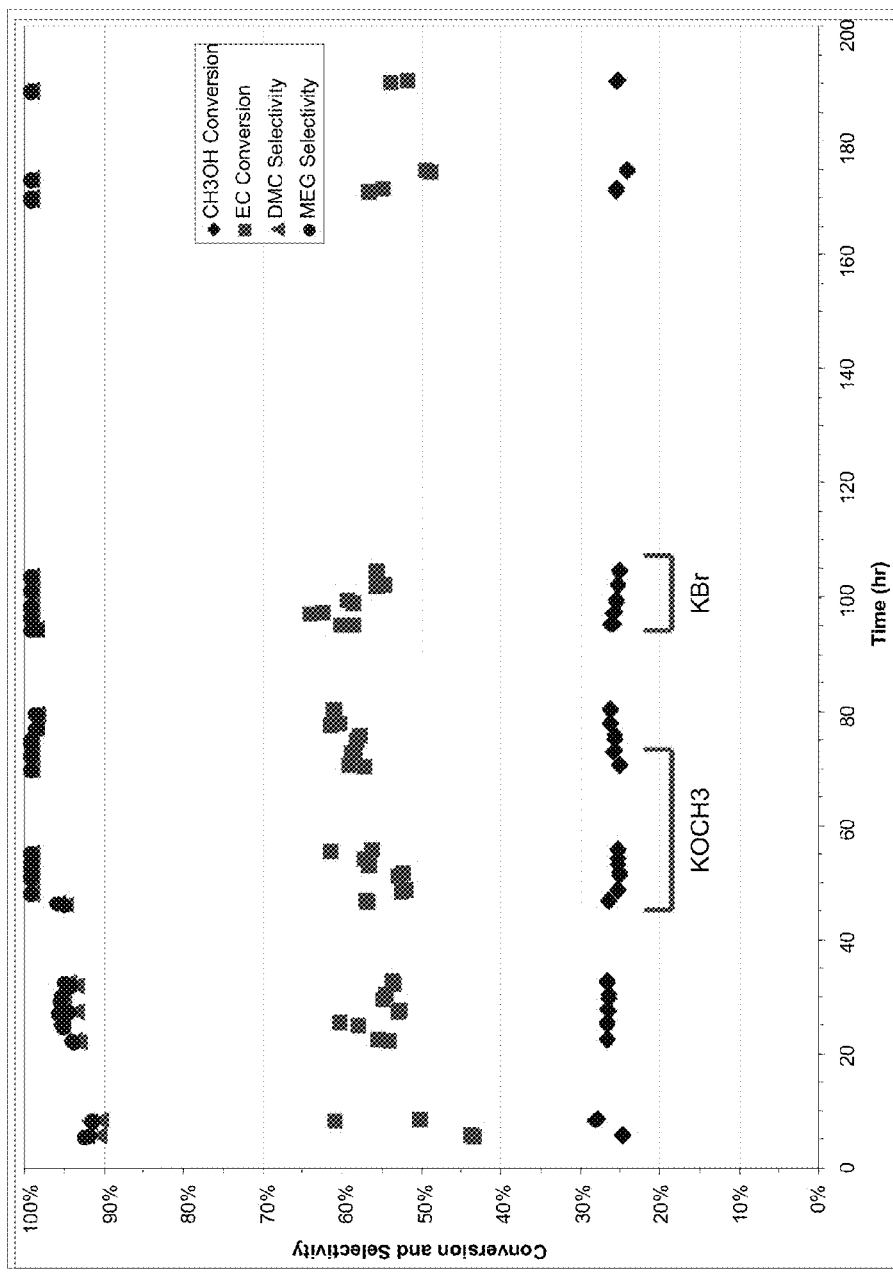
FIG. 3 is a plot of the conversion and selectivity of ethylene carbonate to dimethyl carbonate and ethylene glycol in a transesterification reaction using an ion exchange resin wherein $KOCH_3$ and KBr are each introduced into the reaction.

FIG. 3 shows the effect of $KOCH_3$ and KBr on the transesterification catalyst. The $KOCH_3$ and KBr were each added to the feed in an amount of 0.2 wt. %. As can be seen, the presence of $KOCH_3$ in the feed did not affect the catalyst performance at all. The presence of KBr resulted in a slight decrease in catalyst activity.

Figure 4:
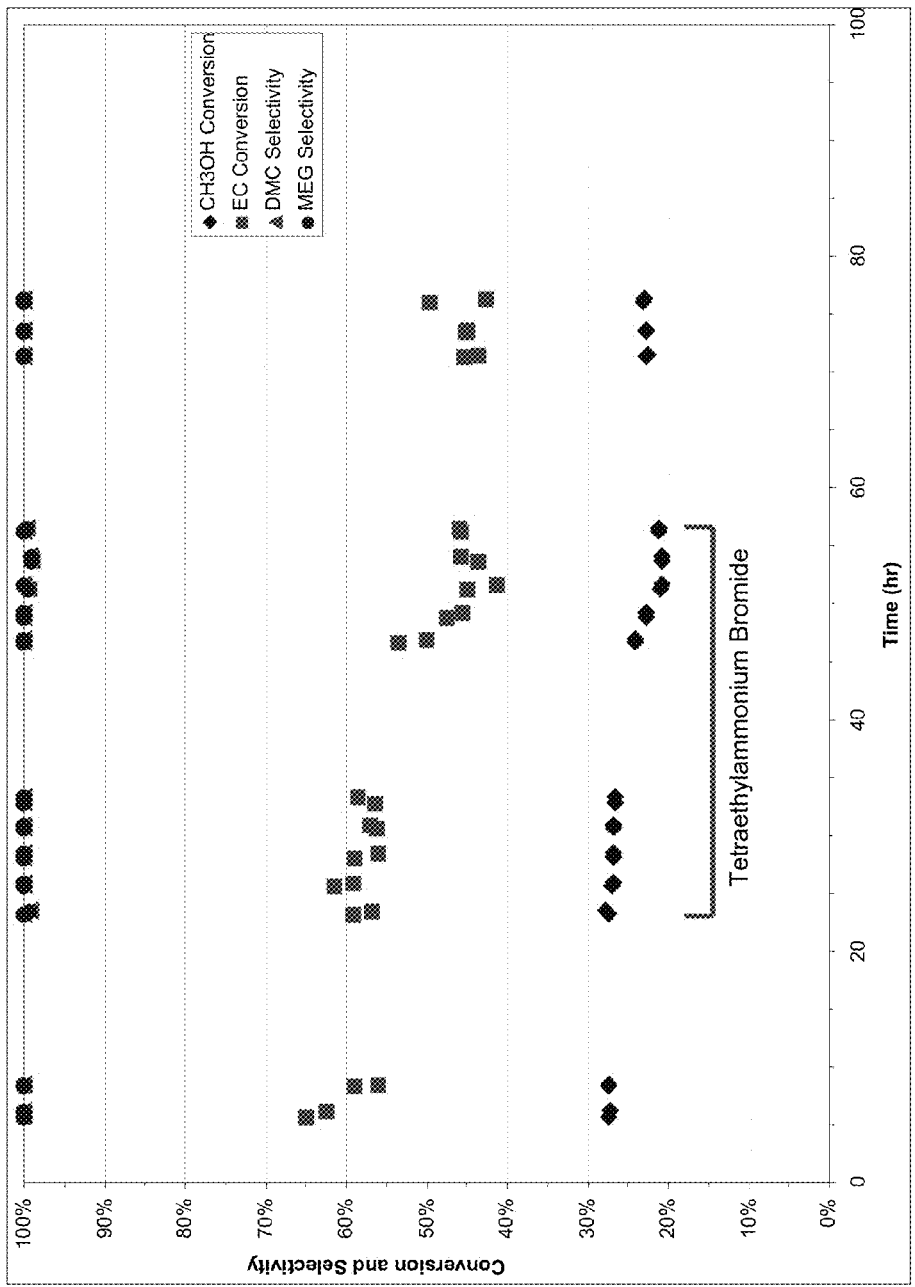
FIG. 4 is a plot of the conversion and selectivity of ethylene carbonate to dimethyl carbonate and ethylene glycol in a transesterification reaction using an ion exchange resin wherein an organic bromide is introduced into the reaction.

FIG. 4 shows the effect of the organic bromide of tetraethylammonium bromide on the transesterification catalyst. The organic bromide was added to the feed in an amount of 0.2 wt. %. As can be seen, the presence of the organic bromide caused a continuing decrease of the catalyst activity until it was removed from the feed. Additionally, the catalyst activity did not improve with the fresh feed without any added organic bromide.

Example 2

The following is an example of a regeneration procedure for an ion exchange resin, such as that of Example 1, containing chloride. The resins were transferred to a graduated cylinder to measure the amount of resin. This was then transferred to an 18 inch glass chromatography column having an 1 inch inner diameter with a Teflon stopcock at the bottom. A reservoir of 1 L or 2 L was connected to the column. After being allowed to settle, the resins are washed with 1000 ml of DI water (≥17 MΩ-cm at 25° C.) per 100 ml of resin. The DI water was gently poured on the top of the resin and the DI water was allowed to flow over the resin. The flow of the DI water was adjusted to about 7-9 ml/min, and thus the total time for washing a batch of 100 ml resins took about 2 hours.

The washed resin was then treated with about a ten-fold excess (by mole) amount of 1 M NaHCO$_3$ solution that was made by dissolving an appropriate amount of NaHCO$_3$ in DI water. For a typical batch of 100 ml resin, 1000 ml of the ion exchange solution was used. The charging and flow control of the ion exchange solution was the same as the washing, described previously.

After completion of the exchange, the resin was again washed with 1000 ml of DI water as described previously.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of preparing a dialkyl carbonate and diol products in an integrated process comprising:
reacting an alkylene oxide with carbon dioxide in the presence of a non-halide-containing homogeneous carbonation catalyst in a first reaction zone to form a crude cyclic carbonate product; and
introducing the crude cyclic carbonate product from the first reaction zone along with an aliphatic monohydric alcohol to a second reaction zone containing a transesterification catalyst comprised of a strongly basic Type I ion exchange resin in gel form of polystyrene crosslinked with divinyl benzene having from about 4% to about 8% crosslinking, and from about 40% to about 60% water retention, the ion exchange resin including at least one of quaternary ammonium groups or quaternary phosphonium groups, the transesterification catalyst being configured as substantially spherical beads having a particle size of from about 0.2 mm to about 1.5 mm and allowing the cyclic carbonate product and monohydric alcohol to react under reaction conditions to form the dialkyl carbonate and diol products
wherein
the non-halide-containing homogeneous carbonation catalyst comprises inorganic compounds selected from the group consisting of hydroxides, carbonates, and bicarbonates of alkali metals,
or
organic compounds selected from the group consisting of alkali methoxides and alkali ethoxides.

2. The method of claim 1, wherein:
the alkylene oxide has the formula

wherein R1 and R$_2$ are independently from one another a —(CH$_2$)m- group, wherein m is an integer of from 1 to 3.

3. The method of claim 2, wherein m is an integer of from 1 to 2.

4. The method of claim 1, wherein:
the aliphatic monohydric alcohol is a C$_1$ to C$_5$ aliphatic monohydric alcohol.

5. The method of claim 1, wherein:
the alkylene oxide is ethylene oxide.

6. The method of claim 1, wherein:
the monohydric alcohol is methanol.

7. The method of claim 1, wherein:
the alkylene oxide is ethylene oxide and the aliphatic monohydric alcohol is methanol, and wherein the dialkyl carbonate includes dimethyl carbonate and the diol includes monoethylene glycol.

8. The method of claim 1, wherein:
the non-halide-containing homogeneous catalyst is selected from at least one of KOH, K$_2$CO$_3$, and KHCO$_3$, potassium methoxide (KOCH$_3$), and potassium ethoxide (KOC$_2$H$_5$).

9. The method of claim 1, wherein:
the non-halide-containing homogeneous catalyst is used in an amount of from about 0.01% to about 5% by weight of alkylene oxide that is introduced into the first reaction zone.

10. The method of claim 1, wherein:
the molar ratio of aliphatic monohydric alcohol to the crude cyclic carbonate product introduced into the second reaction zone is from about 1.5:1 to about 3:1.

11. The method of claim 1, wherein:
the ion exchange resin includes an anion selected from the group consisting of bicarbonate, bisulfite, metalate, carboxylate, and halide.

12. The method of claim 1, further comprising:
removing unreacted alkylene oxide, unreacted carbon dioxide, or both, from said crude cyclic carbonate product prior to introducing product from the first reaction zone to the second reaction zone.

13. The method of claim 1, wherein the non-halide-containing homogeneous catalyst is potassium methoxide (KOCH$_3$).

* * * * *